US006913678B2

(12) United States Patent
Yamada et al.

(10) Patent No.: US 6,913,678 B2
(45) Date of Patent: Jul. 5, 2005

(54) GAS SENSOR

(75) Inventors: Hirokazu Yamada, Nagoya (JP); Takashi Kojima, Kasugai (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/291,835

(22) Filed: Nov. 12, 2002

(65) Prior Publication Data
US 2003/0094368 A1 May 22, 2003

(30) Foreign Application Priority Data

Nov. 20, 2001 (JP) .................................. 2001-354967
Sep. 27, 2002 (JP) .................................. 2002-283916

(51) Int. Cl.[7] ........................................... G01N 27/407
(52) U.S. Cl. ..................................... 204/424; 204/428
(58) Field of Search ................................ 204/421–429

(56) References Cited

U.S. PATENT DOCUMENTS 4,310,401 A * 1/1982 Stahl
4,526,672 A * 7/1985 Reed
4,569,748 A * 2/1986 Yamakawa et al. ......... 204/429
4,802,369 A * 2/1989 Morii ........................... 73/116
5,585,547 A * 12/1996 Kim et al. .................. 73/31.05
5,688,390 A   11/1997 Yamauchi et al.

FOREIGN PATENT DOCUMENTS

JP        8-193971        7/1996

OTHER PUBLICATIONS

Metals Handbook, Desk Edition (2nd), by ASM International, 1998, pp. 76 and 611.*
Copper and Copper Alloys, ASM Specialty Handbook, 2001, pp. 562 and 563.*
ASM Metals Reference Book, 3rd Edition, 1993, pp. 226, 369, and 464.*

* cited by examiner

Primary Examiner—Kaj K. Olsen
(74) Attorney, Agent, or Firm—Nixon & Vanderhye PC

(57) ABSTRACT

An insulator, airtightly supported via an annular metallic packing on a cylindrical housing, has a small-diameter portion and a large-diameter portion. A tapered surface extends in a radially outer direction from a small-diameter cylindrical surface to a large-diameter cylindrical surface. A receiving surface, formed on an inside wall of the housing, supports the tapered surface via the metallic packing. The tapered surface is brought into line contact with the metallic packing at its outer or inner circumferential portion.

12 Claims, 12 Drawing Sheets

GAS SENSOR

BACKGROUND OF THE INVENTION

The present invention relates to a gas sensor installed in an exhaust passage of an internal combustion engine to measure the concentration of a specific gas.

An automotive vehicle engine is equipped with a gas sensor to measure an oxygen concentration or a NOx concentration in an exhaust gas emitted from this engine. The detected gas concentration is used to control the combustion of the engine.

For example, the gas sensor has a gas sensing element extending in a longitudinal direction, a cylindrical insulator having a through hole into which the gas sensing element is airtightly inserted, and a cylindrical housing airtightly supporting the insulator via an annular metallic packing.

A measured gas cover, attached to a distal end side of the housing, defines a space into which the measured gas is introduced. A distal end of the gas sensing element is exposed to a measured gas atmosphere provided inside this cover. An air side cover, attached to a proximal end side of the housing, defines a space into which the air is introduced to provide an air atmosphere.

The clearance between the gas sensing element and the insulator is airtightly sealed. Similarly, the clearance between the insulator and the housing is airtightly sealed.

The gas sensing element has a measured gas side electrode exposed to the gas stored in the measured gas atmosphere and a reference electrode exposed to the air. An ion current or an electric potential difference occurring between the measured gas side electrode and the reference electrode represents the concentration of a specific gas to be measured in the exhaust gas.

According to this arrangement, to assure accurate detection of the specific gas, it is important to provide a reliable sealing for completely separating the measured gas atmosphere from the air atmosphere.

One of the key portions to be surely sealed in the gas sensor is the interface between the insulator and the housing.

FIG. 16 shows a sealing arrangement between the insulator and the housing of a conventional gas sensor. According to this arrangement, an annular metallic packing 1011 interposed between a tapered surface 1033 of an insulator 1003 and a receiving surface 1103 of the housing 1010 determines the sealing property between the insulator 1003 and the housing 1010.

The metallic packing 1011 is brought into face-to-face contact with the receiving surface 1103 and with the tapered surface 1033. A lower surface 1112 of the metallic packing 1011 entirely contacts with the receiving surface 1103. An upper surface 1111 of the metallic packing 1011 entirely contacts with the tapered surface 1033.

However, the tapered surface 1033 of the insulator 1003 has a significant undulation which will give adverse influence to the sealing property between the tapered surface 1033 and the metallic packing 1011.

To compensate this drawback, an additional sealing member such as a power sealing material was conventionally used.

SUMMARY OF THE INVENTION

In view of the above-described problems, the present invention has an object to provide a gas sensor capable of assuring reliable sealing property of a metallic packing interposed between an insulator and a housing without using any additional sealing member.

In order to accomplish the above and other related objects, the present invention provides a first gas sensor including a gas sensing element extending in a longitudinal direction of the gas sensor, a cylindrical insulator having a through hole into which the gas sensing element is airtightly inserted, and a cylindrical housing airtightly supporting the cylindrical insulator via an annular metallic packing. According to the first gas sensor of the present invention, an annular receiving surface is provided on an inner wall of the housing to support the insulator via the metallic packing. The annular receiving surface extends in a radial direction with a predetermined inclined angle with respect to an axis of the gas sensing element. The insulator has a small-diameter portion and a large-diameter portion which are continuously aligned in an axial direction of the insulator. A diameter of the large-diameter portion is larger than a diameter of the small-diameter portion. An outer cylindrical surface of the insulator includes a small-diameter cylindrical surface extending in parallel with the axis of the gas sensing element, a tapered surface, and a large-diameter cylindrical surface extending in parallel with the axis of the gas sensing element. The tapered surface extends in a radially outer direction with a predetermined inclined angle with respect to the axis of the gas sensing element from the small-diameter cylindrical surface to the large-diameter cylindrical surface. An outer circumferential portion of the tapered surface is brought into line contact with the metallic packing when the receiving surface of the housing supports the tapered surface via the metallic packing.

The present invention provides a second gas sensor including a gas sensing element extending in a longitudinal direction of the gas sensor, a cylindrical insulator having a through hole into which the gas sensing element is airtightly inserted, and a cylindrical housing airtightly supporting the cylindrical insulator via an annular metallic packing. According to the second gas sensor, an annular receiving surface is provided on an inner wall of the housing to support the insulator via the metallic packing. The annular receiving surface extends in a radial direction with a predetermined inclined angle with respect to an axis of the gas sensing element. The insulator has a small-diameter portion and a large-diameter portion which are continuously aligned in an axial direction of the insulator. A diameter of the large-diameter portion is larger than a diameter of the small-diameter portion. An outer cylindrical surface of the insulator includes a small-diameter cylindrical surface extending in parallel with the axis of the gas sensing element, a tapered surface, and a large-diameter cylindrical surface extending in parallel with the axis of the gas sensing element. The tapered surface extends in a radially outer direction with a predetermined inclined angle with respect to the axis of the gas sensing element from the small-diameter cylindrical surface to the large-diameter cylindrical surface. An inner circumferential portion of the tapered surface is brought into line contact with the metallic packing when the receiving surface of the housing supports the tapered surface via the metallic packing.

The present invention provides a third gas sensor including a gas sensing element extending in a longitudinal direction of the gas sensor, a cylindrical insulator having a through hole into which the gas sensing element is airtightly inserted, and a cylindrical housing airtightly supporting the cylindrical insulator via an annular metallic packing. According to the third gas sensor, an annular receiving surface is provided on an inner wall of the housing to support the insulator via the metallic packing. The annular receiving surface extends in a radial direction with a predetermined inclined angle with respect to an axis of the gas sensing element. The insulator has a small-diameter portion and a large-diameter portion which are continuously aligned in an axial direction of the insulator. A diameter of the large-diameter portion is larger than a diameter of the small-diameter portion. An outer cylindrical surface of the insulator includes a small-diameter cylindrical surface extending in parallel with the axis of the gas sensing element, a tapered surface, and a large-diameter cylindrical surface extending in parallel with the axis of the gas sensing element. The tapered surface extends in a radially outer direction with a predetermined inclined angle with respect to the axis of the gas sensing element from the small-diameter cylindrical surface to the large-diameter cylindrical surface. An outer circumferential portion of the tapered surface is brought into line contact with the metallic packing when the receiving surface of the housing supports the tapered surface via the metallic packing. A relationship between the tapered surface and the receiving surface is expressed by $\alpha>\beta$ and $0°<\alpha-\beta\leq40°$ where $\alpha$ represents an open angle of the tapered surface and $\beta$ represents an open angle of the receiving surface.

The outer circumferential portion or the inner circumferential portion of the tapered surface has a better roundness compared with other region of the tapered surface. Accordingly, the outer circumferential portion or the inner circumferential portion of the tapered surface is brought into line contact with the metallic packing, thereby providing an excellent and stable sealing between them.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
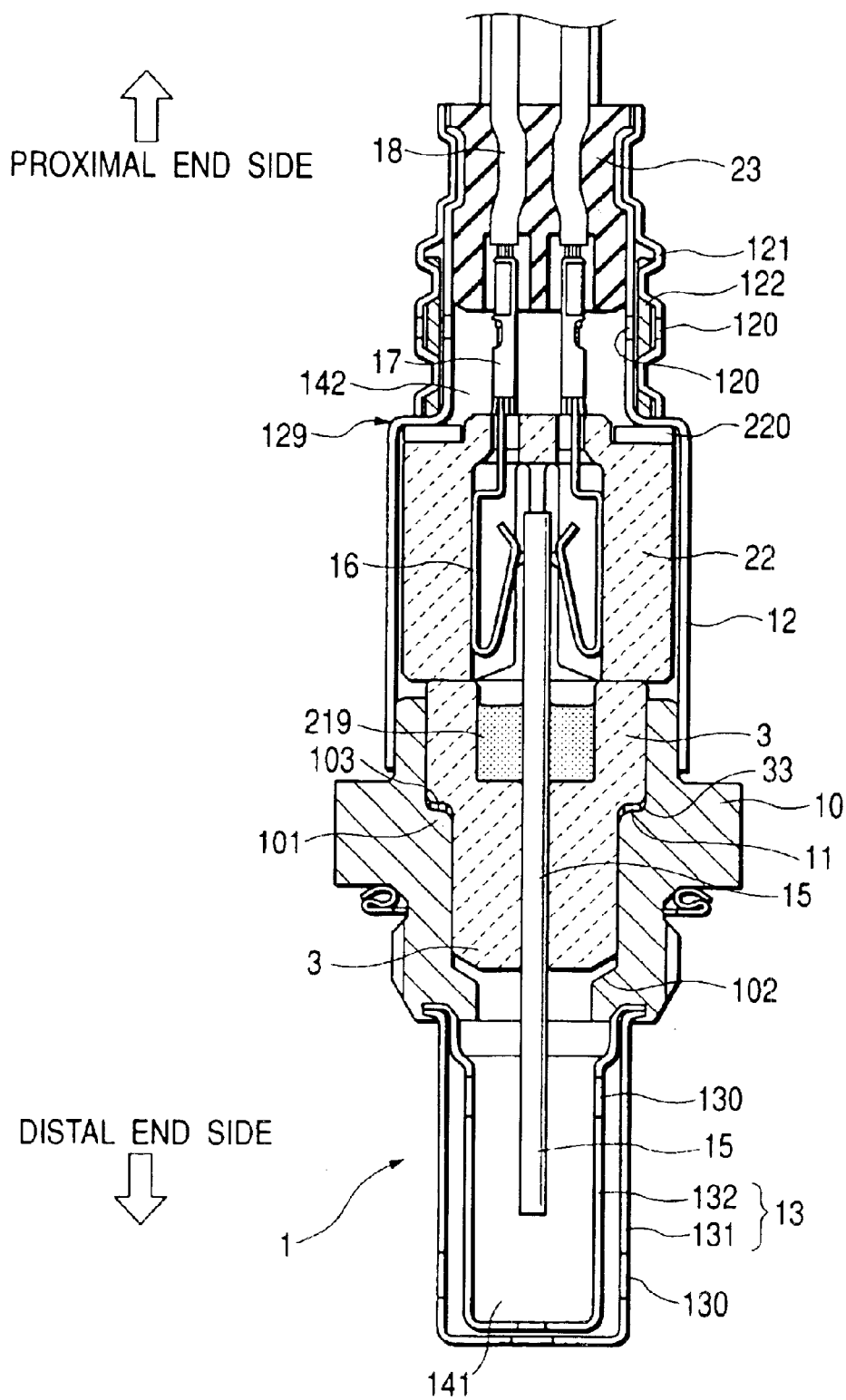
FIG. 1 is a vertical cross-sectional view showing an overall arrangement of a gas sensor in accordance with a first embodiment of the present invention.

Preferred embodiments of the present invention will be explained hereinafter with reference to attached drawings. Identical parts are denoted by the same reference numerals throughout the drawings.

First Embodiment

FIGS. 1 to 8 show a gas sensor in accordance with a first embodiment of the present invention.

A gas sensor 1 of the first embodiment, as shown in FIGS. 1 to 4, has a gas sensing element 15 having a platelike body. The gas sensing element 15 extends in a longitudinal direction of the gas sensor 1. A cylindrical pluglike insulator 3, located adjacent to the gas sensing element 15, has an axial through hole into which the gas sensing element 15 is airtightly coupled. A cylindrical housing 10 receives the cylindrical pluglike insulator 3 via an annular or ringlike metallic packing 11.

The cylindrical housing 10 has an annular receiving surface 103 extending in a radial direction with a predetermined inclined angle with respect to the axis of the gas sensing element 15. The annular metallic packing 11 is placed on the the annular receiving surface 103 of the cylindrical housing 10. The cylindrical pluglike insulator 3 is thus received by the annular receiving surface 103 of the cylindrical housing 10 via the annular metallic packing 11.

The cylindrical pluglike insulator 3 has a small-diameter portion 31 and a large-diameter portion 32 which are coaxial with each other and continuously aligned in the axial direction of the pluglike insulator 3. The large-diameter portion 32 has a diameter larger than that of the small-diameter portion 31. An outer cylindrical surface of the pluglike insulator 3 consists of a small-diameter cylindrical surface 310 extending in parallel with the axis of the gas sensing element 15, a tapered surface 33, and a large-diameter cylindrical surface 320 extending in parallel with the axis of the gas sensing element 15. The tapered surface 33 extends in a radially outer direction from the upper end of the small-diameter cylindrical surface 310 to the lower end of the large-diameter cylindrical surface 320.

The axis of the gas sensing element 15 is identical with a longitudinal center of a cylindrical gas sensor 1. In each of FIGS. 1 to 4, a lower end side of the gas sensor 1 is referred to as a distal end side and an upper end side of the gas sensor 1 is referred to as a proximal end side. A measured gas side cover 13 is attached to the distal end side of the gas sensor 1. Lead wires extend out of the proximal end side of the gas sensor 1.

The receiving surface 103 of the housing 10 supports the tapered surface 33 of the pluglike insulator 3 via the metallic packing 11. The tapered surface 33 is brought into contact with the metallic packing 11 at an outer circumferential portion 331 so as to provide an annular line contact between the tapered surface 33 and the metallic packing 11.

Hereinafter, the gas sensor 1 of the first embodiment will be explained.

The gas sensor 1 is installed in an exhaust passage of an automotive engine to detect an air-fuel ratio based on an oxygen concentration in the exhaust gas. The air-fuel ratio of a gas mixture introduced into a combustion chamber of the automotive engine is controlled based on the detection value of the gas sensor 1.

As shown in FIG. 1, attached to the distal end side of the housing 10 is the measured gas side cover 13 consisting of an outer cover 131 and an inner cover 132 cooperatively constituting a double-layer structure. Each of the covers 131 and 132 has gas holes 130 for introducing the exhaust gas to be measured from the exhaust passage of the automotive engine. The exhaust gas, when introduced via the gas holes 130 into the inner cover 132, forms a measured gas atmosphere 141 to which the distal end of gas sensing element 15 is exposed.

Furthermore, attached to the proximal end side of the housing 10 is an air side cover 12. The air side cover 12 has a proximal end portion around which an outer cover 121 is provided via a water repellent filter 122. Each of the air side cover 12 and the outer cover 121 has air holes 120 for introducing the air from the outside. The air holes 120 are positioned at the portion where the water repellent filter 122 is provided.

The air side cover 12 has a stepped configuration chiefly constituting a large-diameter portion closer to the housing 10 and a small-diameter portion far from the housing 10 continuously formed via a step 129. The air, when introduced via the air holes 120 into the air side cover 12, forms an air atmosphere 142.

The cylindrical housing 10 has two inside cylindrical portions 101 and 102 protruding in the radially inward direction. The receiving surface 103, formed as an upper end annular surface of the inner cylindrical portion 101, supports the tapered surface 33 of the pluglike insulator 3 via the metallic packing 11. The metallic packing 11 is made of a nickel material having a purity of 99%.

The sealing structure in the gas sensor 1, brought by the metallic packing 11 interposed between the tapered surface 33 and the receiving surface 103, airtightly separates the air atmosphere 142 from the measured gas atmosphere 141.

A sleevelike insulator 22, disposed adjacent to the proximal end side of the gas sensor 1, is aligned next to the pluglike insulator 3 in the axial direction of the gas sensing element 15. A disc spring 220 is interposed between an upper end annular surface of the sleevelike insulator 22 and the step 129 of the air side cover 12. A total of four lead terminals 16, located inside the sleevelike insulator 22, provide an electric connection between the platelike gas sensing element 15 and lead wires 18.

The platelike gas sensing element 15 has a multilayered structure and is equipped with a heater element embedded in its laminated body. Although not shown in the drawing, the gas sensing element 15 has a pair of sensor electrodes for taking out a sensing signal and a pair of power electrodes for supplying electric power to the built-in heater. These electrodes, i.e., a total of four electrodes, are connected via the lead terminals 16 to a total of four lead wires 18 extending out of the gas sensor 1.

More specifically, each lead terminal 16 has a proximal end extending upward above the sleevelike insulator 22. The proximal end of each lead terminal 16 is connected to a corresponding lead wire 18 by using a connector 17. An elastic insulating member 23 closes a proximal end opening of the air side cover 12. Each of the lead wires 18 extends in the axial direction across the elastic insulating member 23 and protrudes out of the gas sensor 1.

Figure 2A:
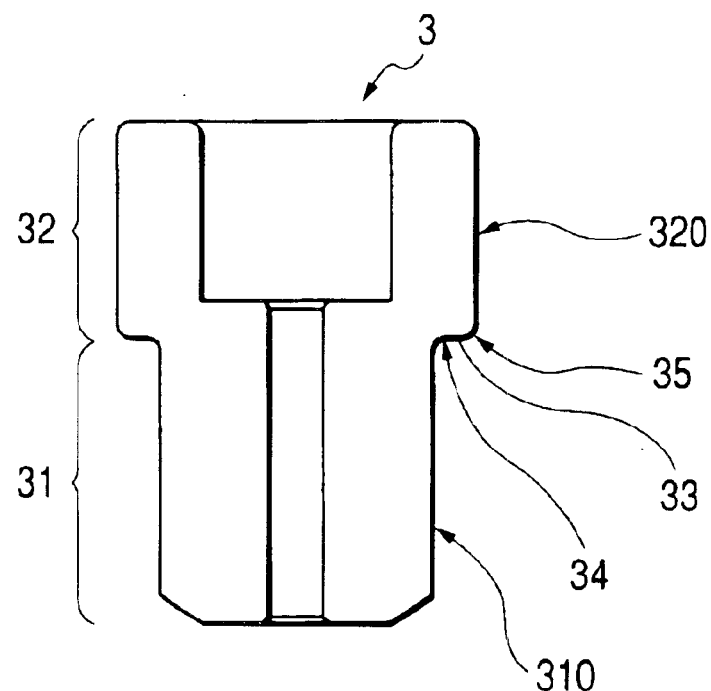
FIG. 2A is an enlarged cross-sectional view showing an insulator located adjacent to a gas sensing element in the gas sensor in accordance with the first embodiment of the present invention.
Figure 3:
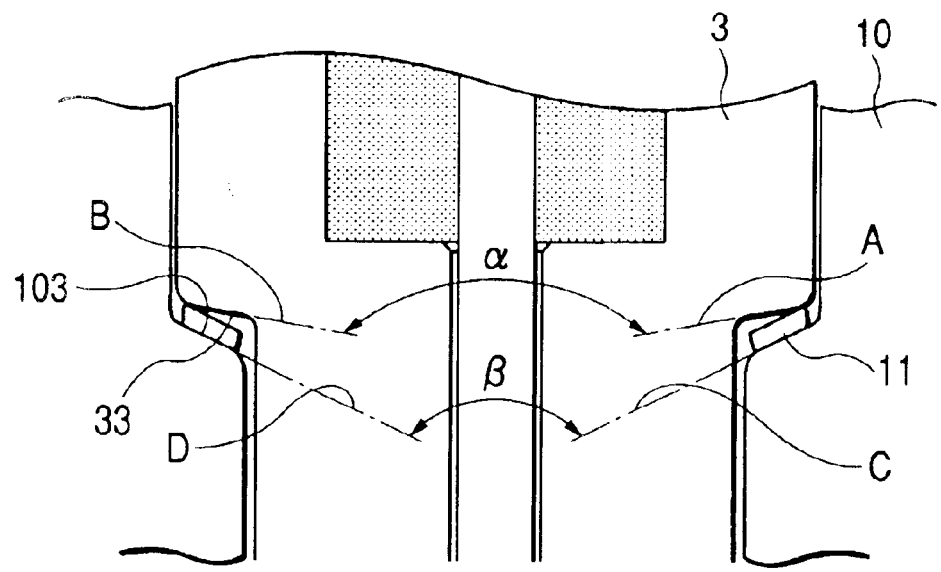
FIG. 3 is an enlarged cross-sectional view showing a relationship between a tapered surface angle $\beta$ and a receiving surface angle $\alpha$ in accordance with the first embodiment of the present invention.
Figure 4:
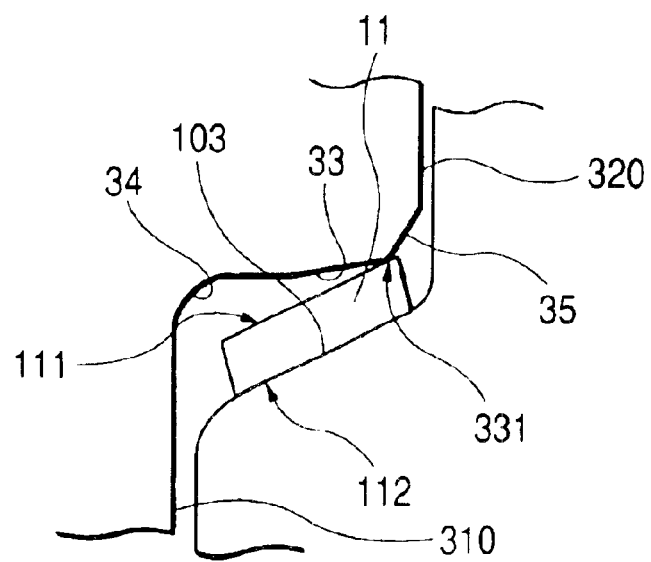
FIG. 4 is an enlarged cross-sectional view showing a sealing structure brought by a metallic packing interposed between the tapered surface and the receiving surface in accordance with the first embodiment of the present invention.

As shown in FIG. 2A, the pluglike insulator 3 has a cylindrical ceramic body consisting of the small-diameter portion 31 positioned at the distal end side and the large-diameter portion 32 positioned at the proximal end side. The large-diameter portion 32 has a diameter larger than that of the small-diameter portion 31. The tapered surface 33 extends in a radially outward direction from the small-diameter portion 31 to the large-diameter portion 32. The tapered surface 33 is continuous with a corner portion 34 provided at an uppermost end of the small-diameter cylindrical surface 310 of the small-diameter portion 31. The corner portion 34 has a curved or round surface. The tapered surface 33 is continuous with a corner portion 35 provided at a lowermost end of the large-diameter cylindrical surface 320 of the large-diameter portion 32. The corner portion 35 is a slant surface being chamferred. As shown in FIGS. 3 and 4, the tapered surface 33 of the pluglike insulator 3 is in a non-parallel relationship with the receiving surface 103 of the housing 10.

More specifically, as shown in FIG. 3, the non-parallel relationship between the tapered surface 33 and the receiving surface 103 can be expressed by an open angle α of the tapered surface 33 and an open angle β and the receiving surface 103. The open angle α of the tapered surface 33, facing toward the proximal end side (i.e., upper direction) of the insulator 3, represents a crossing angle between two (right and left) inclined lines A and B of the tapered surface 33 in the cross-sectional view taken along the axis of the pluglike insulator 3 (i.e., along the axis of the gas sensing element 15). Similarly, the open angle β of the receiving surface 103, facing toward the proximal end side (i.e., upper direction) of the housing 10, represents a crossing angle between two (right and left) inclined lines C and D of the receiving surface 103 in the cross-sectional view taken along the axis of the housing 10 (i.e., along the axis of the gas sensing element 15). According to the above definition, the non-parallel relationship between the tapered surface 33 and the receiving surface 103 is expressed by $\alpha > \beta$ and $\alpha - \beta = 8°$. The angle between the large-diameter cylindrical surface 320 and the tapered surface 33 is larger than 90° (i.e., a <180°). In other words, the tapered surface 33 protrudes outward (i.e., toward the distal end side of the pluglike insulator 3) with respect to the large-diameter portion 32. In this respect, the tapered surface 33 is referred to as being inclined in an axially outward direction.

As shown in FIG. 4, the metallic packing 11 has a lower surface 112 which is brought into face-to-face contact with the receiving surface 103 of housing 10. The metallic packing 11 has an upper surface 111 which is brought into line contact with the outer circumferential portion 331 of the tapered surface 33 of pluglike insulator 3.

Figure 2B:
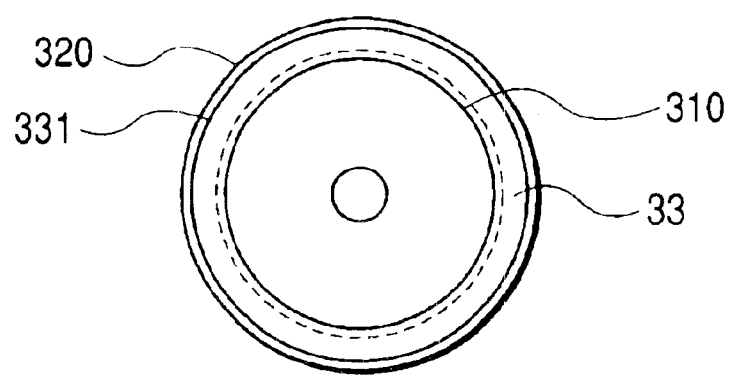
FIG. 2B is an enlarged bottom view showing the insulator shown in FIG. 2A.

Furthermore, as shown in FIG. 2B, the outer circumferential portion 331 has substantially the complete roundness. The roundness will be explained in detail later.

The pluglike insulator 3 has an axially extending through hole into which the platelike gas sensing element 15 is inserted. The axially extending through hole is radially enlarged at the large-diameter portion 32 (i.e., at the proximal end side) of the pluglike insulator 3 so that a sufficient space is provided between the inner wall of pluglike insulator 3 and the outer surface of platelike gas sensing element 15. The space between the pluglike insulator 3 and the gas sensing element 15 is filled with a sealing member 219 which is made of a glass material. The sealing member 219 airtightly separates the air atmosphere 142 from the measured gas atmosphere 141.

Installation of the gas sensor 1 in accordance with this embodiment will be explained hereinafter.

First, the platelike gas sensing element 15 is inserted into the axially extending hole of the pluglike insulator 3. The sealing member 219 is stuffed into the space between the inside wall of insulator 3 and the outer surface of gas sensing element 15. With the sealing member 219, the insulator 3 and the gas sensing element 15 are firmly fixed to each other. Next, the metallic packing 11 is disposed on the receiving surface 103 of the housing 10. The pluglike insulator 3 is inserted into the housing 10 so that the tapered surface 33 of pluglike insulator 3 is supported via the metallic packing 11 on the receiving surface 103 of the housing 10.

The sleevelike insulator 22, accommodating the lead terminals 16, and the disc spring 220 are disposed inside the air side cover 12. In this case, respective lead terminals 16 are connected to the corresponding lead wires 18 so as to provide electric paths extending to the electrode terminals of the platelike gas sensing element 15.

Then, while a pressing force is applied on the step 129 of the air side cover 12, the distal end (i.e., lower end) of the sleevelike insulator 22 is brought into contact with the distal end (i.e., upper end) of pluglike insulator 3. The pressing force applied on the step 129 is transmitted to the pluglike insulator 3 and thus serves as a force for ensuring the sealing of the metallic packing 11 interposed between the tapered surface 33 and the receiving surface 103. According to this embodiment, a pressing force of 5.89 kN acts on the metallic packing 11 interposed between the tapered surface 33 and the receiving surface 103.

Then, the distal end opening of air side cover 12 is coupled around the proximal end of the housing 10. The overlapped portion is welded.

Then, the measured gas side cover 13 is attached and welded to the distal end of the housing 10.

During the installation of the gas sensor 1, the metallic packing 11 is forcibly depressed against the tapered surface 33 of pluglike insulator 3. With this depressing operation, the metallic packing 11 deforms so as to fit the undulation of the receiving surface 103 of housing 10. Therefore, the metallic packing 11 is brought into face-to-face contact with the receiving surface 103 of housing 10.

On the other hand, the tapered surface 33 of pluglike insulator 3 is brought into line contact with the metallic packing 11 along the outer circumferential portion 331.

The roundness of the outer circumferential portion 331 of pluglike insulator 3 was experimentally measured in the following manner.

First, a total of 22 test samples of the above-described pluglike insulator 3 according to the first embodiment were prepared. For each test sample, measurement was performed to measure a maximum diameter and a minimum diameter of the outer circumferential portion 331 (refer to FIG. 2B).

Figure 5:
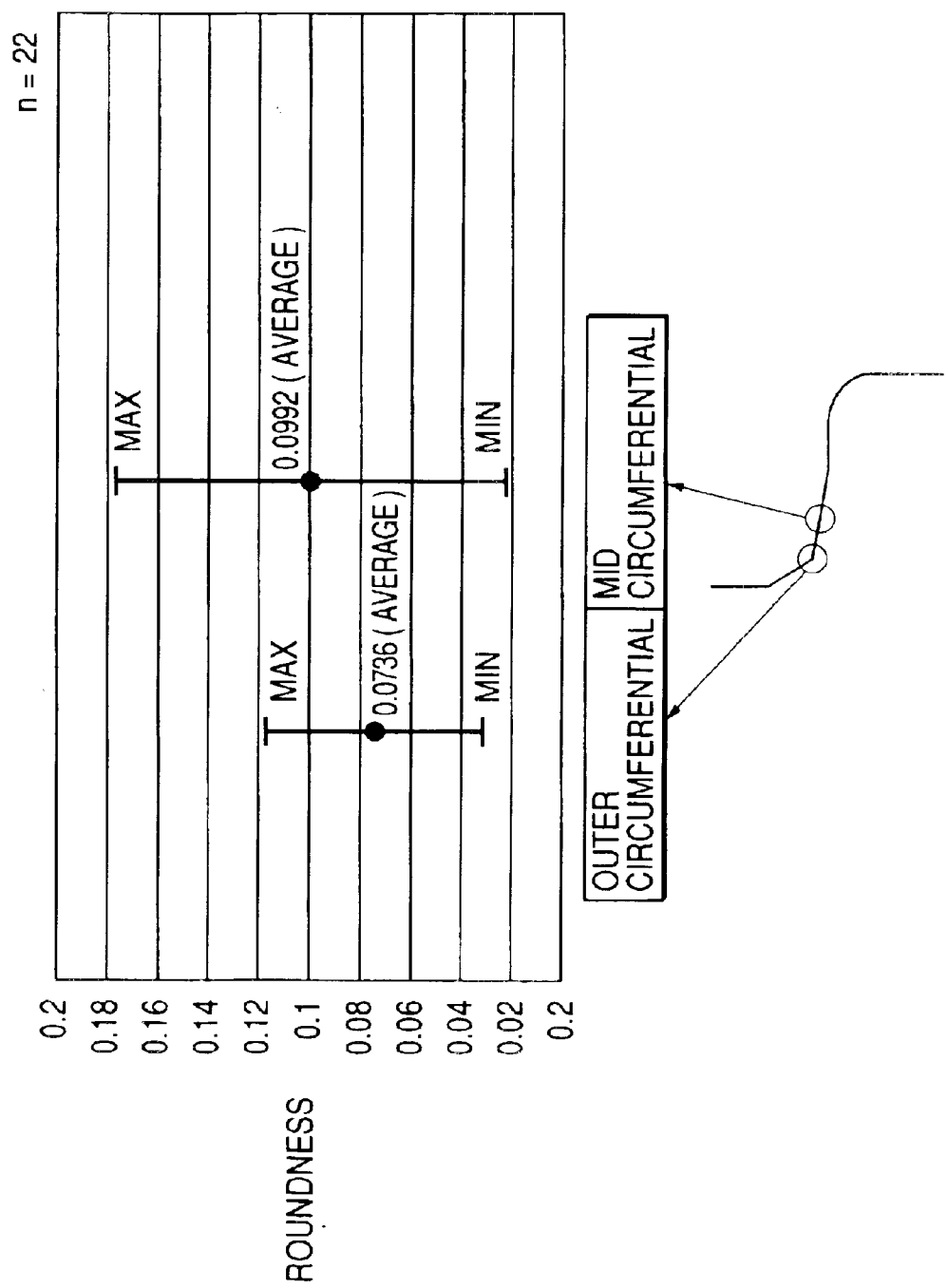
FIG. 5 is a graph showing the roundness of the tapered surface of the insulator located adjacent to the gas sensing element at an outer circumferential portion and at a mid circumferential portion in accordance with the first embodiment of the present invention.

FIG. 5 is a graph showing the roundness (i.e., calculated result with respect to the measured sizes) of the outer circumferential portion 331 based on the tested samples. FIG. 5 also shows the roundness of a mid circumferential portion (i.e., a reference circular portion passing the radial center) of the tapered surface 33.

As understood from the result shown in FIG. 5, the roundness of the outer circumferential portion 331 has a small dispersion. On the other hand, the roundness of the mid circumferential portion passing the radial center of the tapered surface 33 has a large dispersion.

Next, the sealing property of the gas sensor 1 according to this embodiment was measured in the following manner.

Figure 6:
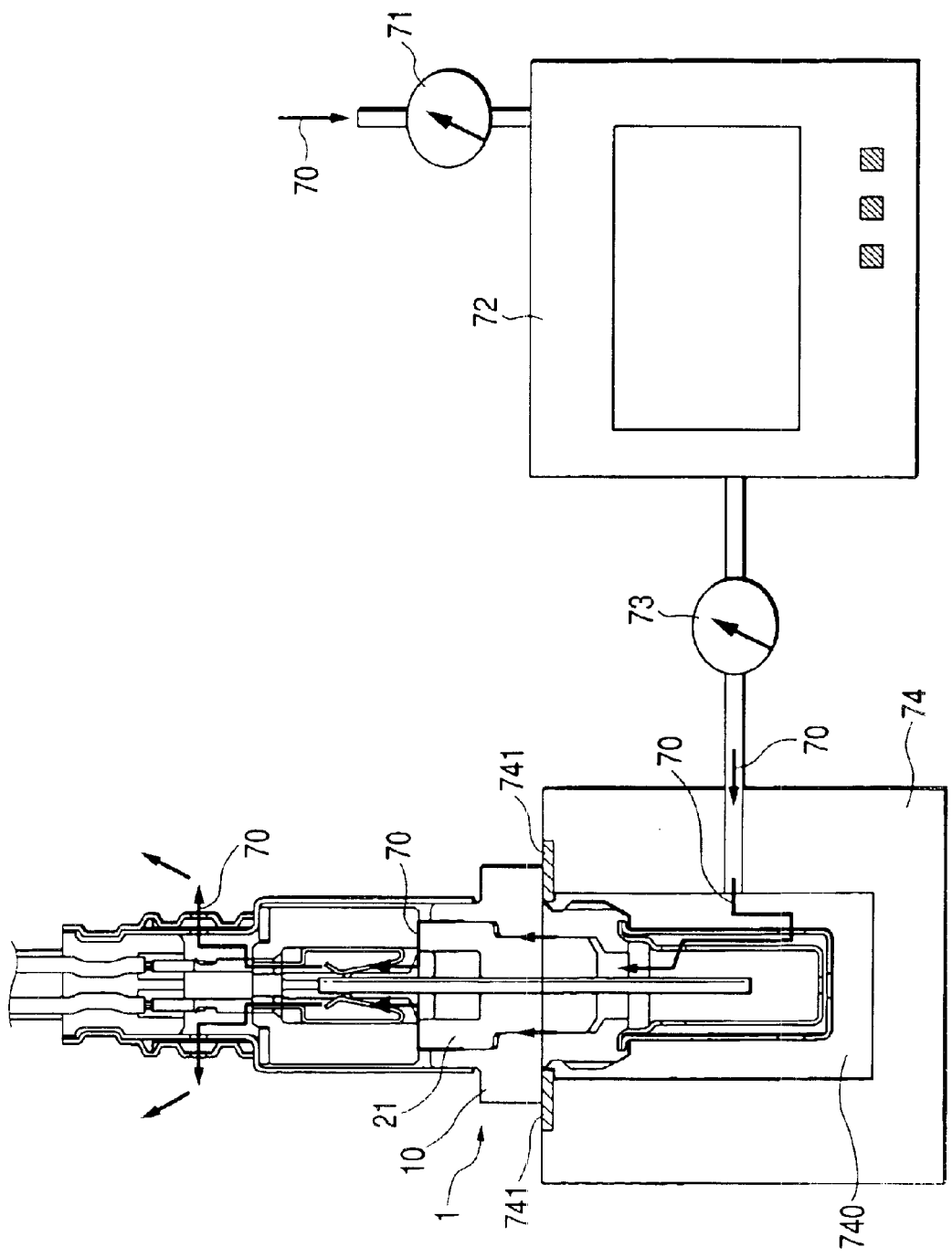
FIG. 6 is a view explaining a testing apparatus for measuring airtightness of the gas sensor in accordance with the first embodiment of the present invention.

Each tested gas sensor 1 was installed in a measuring apparatus shown in FIG. 6 to measure the leakage of air or gas between the air atmosphere 142 and the measured gas atmosphere 141.

The measuring apparatus shown in FIG. 6 chiefly consists of a leakage amount measuring device 72 equipped with a valve 71 which controls the air amount supplied to the tested gas sensor 1, a gas sensor holding jig 74 for holding the tested gas sensor 1 in an upright position and having an inside space for hermetically accommodating the proximal end side of the tested gas sensor 1, and a valve 73 provided in a pipe connecting the leakage amount measuring device 72 and an inside space of the gas sensor holding jig 74.

The following is the detailed measuring method.

The tested gas sensor 1 is installed on the gas sensor holding jig 74 to airtightly separate the air atmosphere 142 and the measured gas side atmosphere 141. Under this condition, both of the valves 71 and 73 are opened to supply the air into the inside space (i.e., air reservoir 740) of the gas holding jig 74. A rubber packing 741, provided along an upper opening periphery of the air reservoir 740, airtightly seals the clearance between the housing 10 of the tested gas sensor 1 and the gas holding jig 74.

When the sealing between the pluglike insulator 3 and the metallic packing 11 is insufficient, the air introduced into the air reservoir 740 leaks along the arrow shown in FIG. 6 while the pressure in the air reservoir 740 decreases with elapsed time.

This measuring apparatus was used to detect a pressure reduction occurring in the air reservoir 740 at the time passage of 10 seconds after a predetermined amount of air (4 atms) was supplied into the air reservoir 740.

The leakage amount (defined by the unit of cm³/min) was obtained based on the detected pressure reduction in the air reservoir 740. Prior to this measurement, the fact that no leakage of air or gas occurs in other portions was checking and confirmed.

The test samples of the gas sensor 1 used in the above-described leakage measurement are classified into six types of 145°, 149°, 152°, 155°, 159°, and 164° with respect to the open angle β of the receiving surface 103, although the open angle α of the tapered surface 33 is fixed to 160°.

Figure 7:
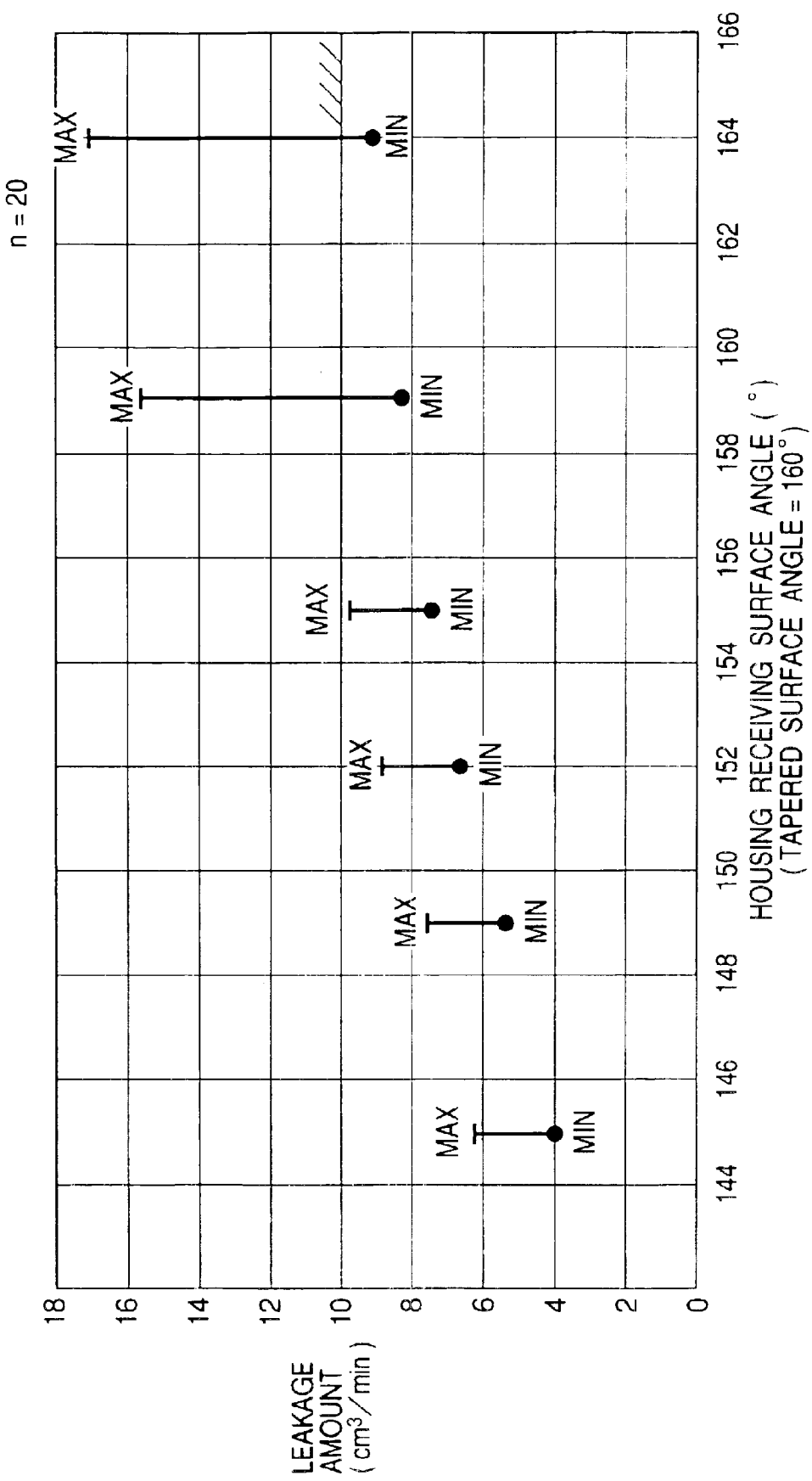
FIG. 7 is a graph showing the measured airtightness of the gas sensor in accordance with the first embodiment of the present invention.

A total of 20 test samples were prepared for each type with respect to the open angle β of the receiving surface 103. FIG. 7 shows the result of the leakage measurement.

As shown in FIG. 7, the leakage amount can be suppressed to a level less than 10 cm³/min when the difference between the open angle α of the tapered surface 33 and the open angle β of the received surface 103 exceeds 5°. It is checked beforehand that no adverse influence is given to the gas sensing performance when the leakage amount is less than 10 cm³/min.

The above-described embodiment of the present invention has the following functions and effects.

The gas sensor 1 has the tapered surface 33 with the outer circumferential portion 331. The outer circumferential portion 331 has a better roundness compared with other region of the tapered surface 33 (refer to FIG. 5). The outer circumferential portion 331 is brought into line contact with the metallic packing 11, thereby providing an excellent and stable sealing between them.

The open angle α of the tapered surface 33 is 160°. The open angle β of the receiving surface 103 is 152°. An angular difference (α–β) between the tapered surface 33 and the receiving surface 103 is 8°. The angle between the large-diameter cylindrical surface 320 and the tapered surface 33 is larger than 90° (i.e., α<180°) so that the tapered surface 33 protrudes outward (i.e., toward the distal end side of the pluglike insulator 3) with respect to the large-diameter portion 32. The tapered surface 33 thus inclines in the axially outward direction with respect to the large-diameter portion 32. The tapered surface 33 of the insulator 3 is in a non-parallel relationship with the receiving surface 103 of the housing 10.

Thus, the present invention assures excellent sealing property brought by a stable line contact between the tapered surface 33 and the metallic packing 11.

As described above, the present invention provides a gas sensor capable of assuring excellent sealing property between the pluglike insulator and the housing by using only the metallic packing.

Figure 8:
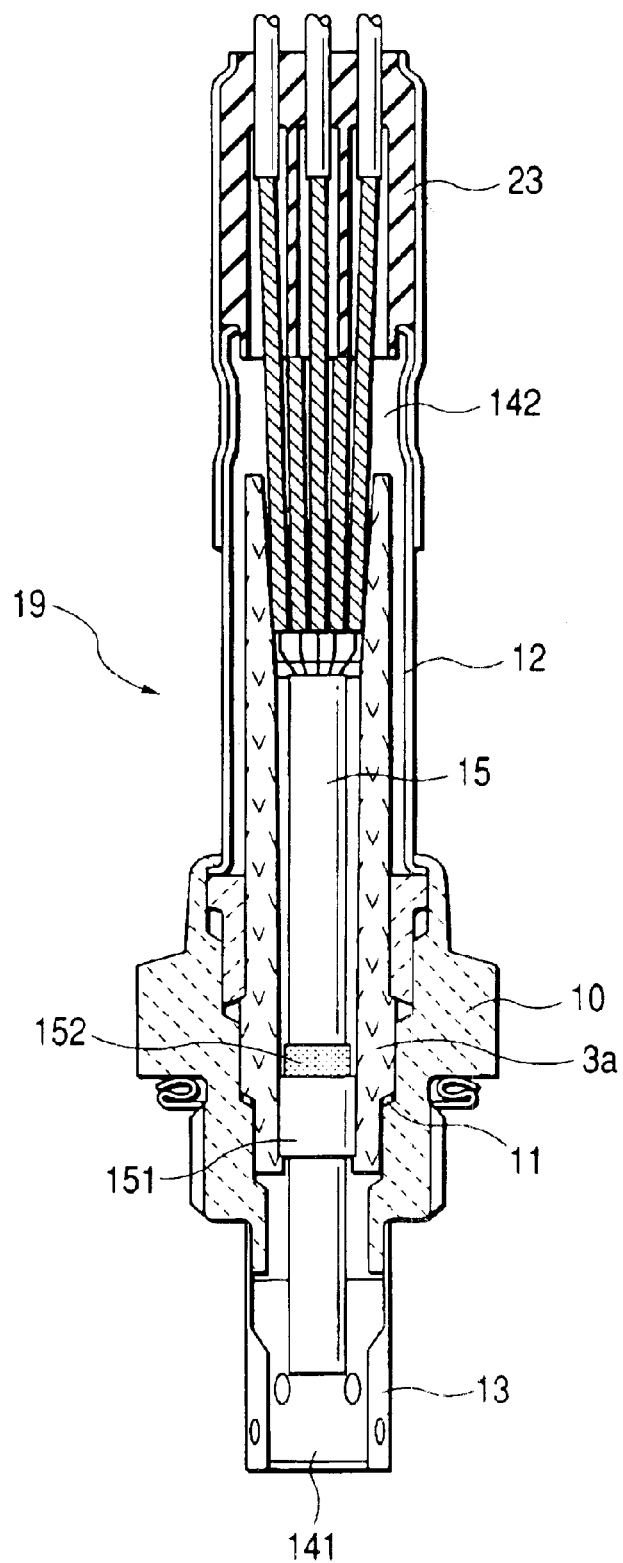
FIG. 8 is a vertical cross-sectional view showing an overall arrangement of a modified gas sensor in accordance with the first embodiment of the present invention.

FIG. 8 shows another gas sensor 19 in accordance with the first embodiment. The gas sensor 19 shown in FIG. 8 is different from the gas sensor 1 shown in FIG. 1 in that the pluglike insulator 3 and the sleevelike insulator 22 are modified into a single sleevelike insulator 3a. Two rings 151 and 152, continuously and serially disposed in the axial direction of the gas sensing element 15, are coupled around the gas sensing element 15 to provide an airtight sealing between the inner wall of the sleevelike insulator 3a and the gas sensing element 15.

The gas sensor 19 shown in FIG. 8 is identical with the embodiment shown in FIG. 1 in that the tapered surface of the sleevelike insulator 3a is supported via the metallic packing 11 on the receiving surface of the housing 10.

The rest of the arrangement of gas sensor 19 is similar to that of the gas sensor 1 shown in FIG. 1. Thus, the gas sensor 19 shown in FIG. 8 assures excellent sealing property between the sleevelike insulator 3a and the housing 10 which is brought by a stable line contact between the metallic packing 11 and the outer circumferential portion of the tapered surface of the sleevelike insulator 3a.

Second Embodiment

The gas sensor in accordance with a second embodiment is structurally similar to the gas sensor in accordance with the first embodiment, but is different in that the tapered surface inclines in an axially inward direction with respect to the large-diameter portion 32.

Figure 9:
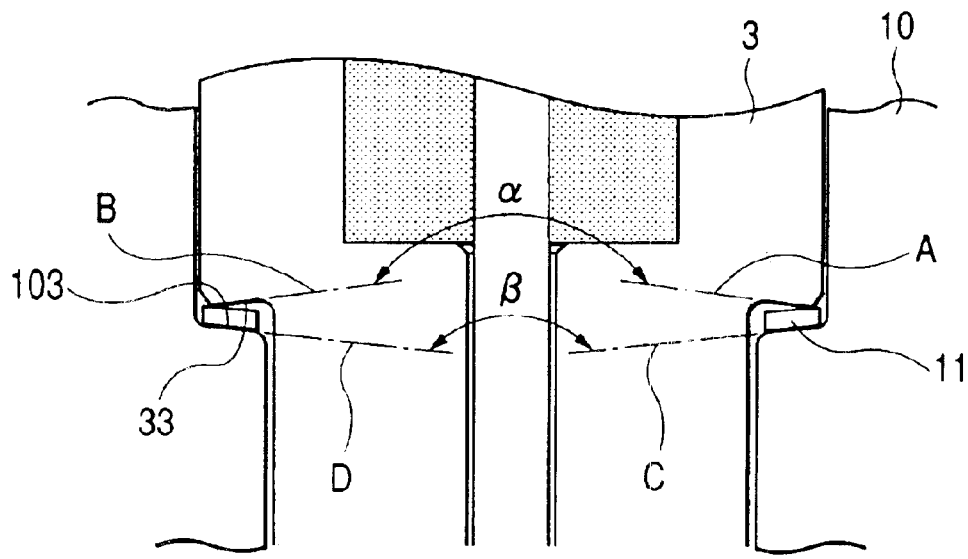
FIG. 9 is an enlarged cross-sectional view showing a relationship between the tapered surface angle $\beta$ and the receiving surface angle $\alpha$ in accordance with a second embodiment of the present invention.
Figure 10:
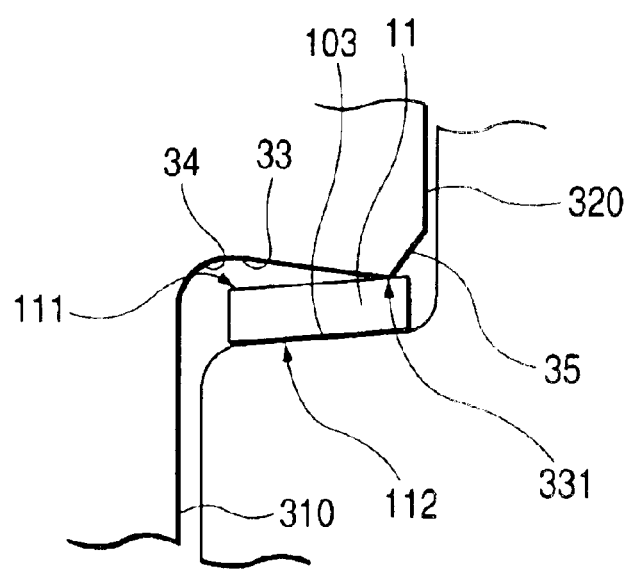
FIG. 10 is an enlarged cross-sectional view showing a sealing structure brought by a metallic packing interposed between the tapered surface and the receiving surface in accordance with the second embodiment of the present invention.

As shown in FIGS. 9 and 10, the tapered surface 33 of the pluglike insulator 3 extends from the large-diameter cylindrical surface 320 to the small-diameter cylindrical surface 310. The angle between the large-diameter cylindrical surface 320 and the tapered surface 33 is smaller than 90° (i.e., α>180°). In other words, the tapered surface 33 retracts inward (i.e., toward the proximal end side of the insulator 3) with respect to the large-diameter portion 32. In this respect, the tapered surface 33 is referred to as being inclined in an axially inward direction.

More specifically, as shown in FIG. 9, the tapered surface 33 of the pluglike insulator 3 is in a non-parallel relationship with the receiving surface 103 of the housing 10. The open angle α of the tapered surface 33, facing toward the proximal end side (i.e., upper direction) of the insulator 3, represents a crossing angle between two (right and left) inclined lines A and B of the tapered surface 33 in the cross-sectional view taken along the axis of the pluglike insulator 3 (i.e., along the axis of the gas sensing element 15). Similarly, the open angle β of the receiving surface 103, facing toward the proximal end side (i.e., upper direction) of the housing 10, represents a crossing angle between two (right and left) inclined lines C and D of the receiving surface 103 in the cross-sectional view taken along the axis of the housing 10 (i.e., along the axis of the gas sensing element 15). According to the embodiment shown in FIG. 9, the open angle α of the tapered surface 33 is 200°. The open angle β of the receiving surface 103 is 170°. The non-parallel relationship between the tapered surface 33 and the receiving surface 103 is expressed by α>β and α–β=30°.

As shown in FIG. 10, the metallic packing 11 has a lower surface 112 which is brought into face-to-face contact with the receiving surface 103 of housing 10. The metallic packing 11 has an upper surface 111 which is brought into line contact with an outer circumferential portion 331 of the tapered surface 33 of pluglike insulator 3.

Like the first embodiment shown in FIG. 2B, the outer circumferential portion 331 has substantially the complete roundness.

The rest of the gas sensor in accordance with the second embodiment is substantially the same as that of the gas sensor in accordance with the first embodiment. Thus, the second embodiment brings the same functions and effects as those of the first embodiment.

Third Embodiment

The gas sensor in accordance with a third embodiment is structurally similar to the gas sensor in accordance with the first embodiment, but is different in that an inner circumferential portion of the tapered surface 33 is brought into line contact with the metallic packing 11.

Figure 11:
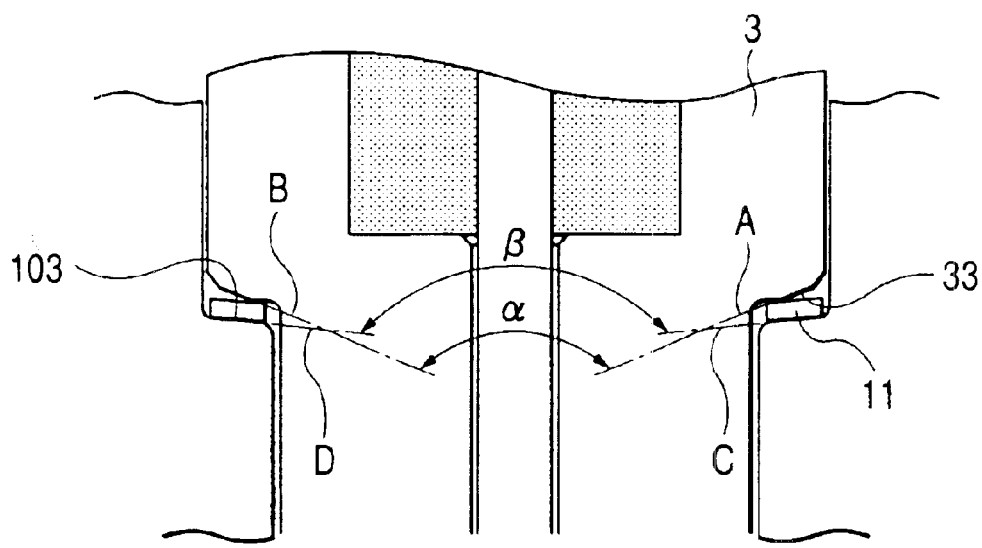
FIG. 11 is an enlarged cross-sectional view showing a relationship between the tapered surface angle $\beta$ and the receiving surface angle $\alpha$ in accordance with a third embodiment of the present invention.
Figure 12:
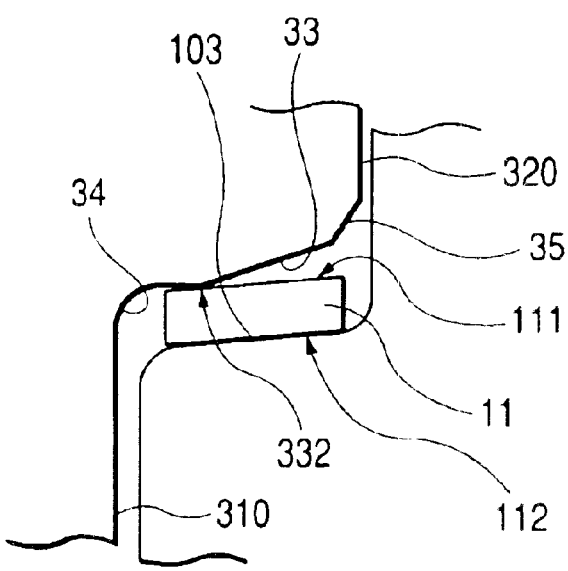
FIG. 12 is an enlarged cross-sectional view showing a sealing structure brought by a metallic packing interposed between the tapered surface and the receiving surface in accordance with the third embodiment of the present invention.

As shown in FIGS. 11 and 12, the tapered surface 33 of the pluglike insulator 3 extends from the large-diameter cylindrical surface 320 to the small-diameter cylindrical surface 310. The angle between the large-diameter cylindrical surface 320 and the tapered surface 33 is larger than 90° (i.e., α<180°). In other words, the tapered surface 33 protrudes outward (i.e., toward the distal end side of the insulator 3) with respect to the large-diameter portion 32. In this respect, the tapered surface 33 is referred to as being inclined in an axially outward direction.

The tapered surface 33 of the pluglike insulator 3 is in a non-parallel relationship with the receiving surface 103 of the housing 10.

More specifically, as shown in FIG. 11, the open angle α of the tapered surface 33, facing toward the proximal end side (i.e., upper direction) of the insulator 3, represents a crossing angle between two (right and left) inclined lines A and B of the tapered surface 33 in the cross-sectional view taken along the axis of the pluglike insulator 3 (i.e., along the axis of the gas sensing element 15). Similarly, the open angle β of the receiving surface 103, facing toward the proximal end side (i.e., upper direction) of the housing 10, represents a crossing angle between two (right and left) inclined lines C and D of the receiving surface 103 in the cross-sectional view taken along the axis of the housing 10 (i.e., along the axis of the gas sensing element 15). According to the embodiment shown in FIG. 11, the open angle α of the tapered surface 33 is 130°. The open angle β of the receiving surface 103 is 160°. The nonparallel relationship between the tapered surface 33 and the receiving surface 103 is expressed by α<β and β−α=30°.

As shown in FIG. 12, the metallic packing 11 has a lower surface 112 which is brought into face-to-face contact with the receiving surface 103 of housing 10. The metallic packing 11 has an upper surface 111 which is brought into line contact with an inner circumferential portion 332 of the tapered surface 33 of pluglike insulator 3.

A total of 22 test samples of the above-described pluglike insulator 3 in accordance with the third embodiment were prepared. For each test sample, measurement was performed to measure a maximum diameter and a minimum diameter of the inner circumferential portion 332.

Figure 13:
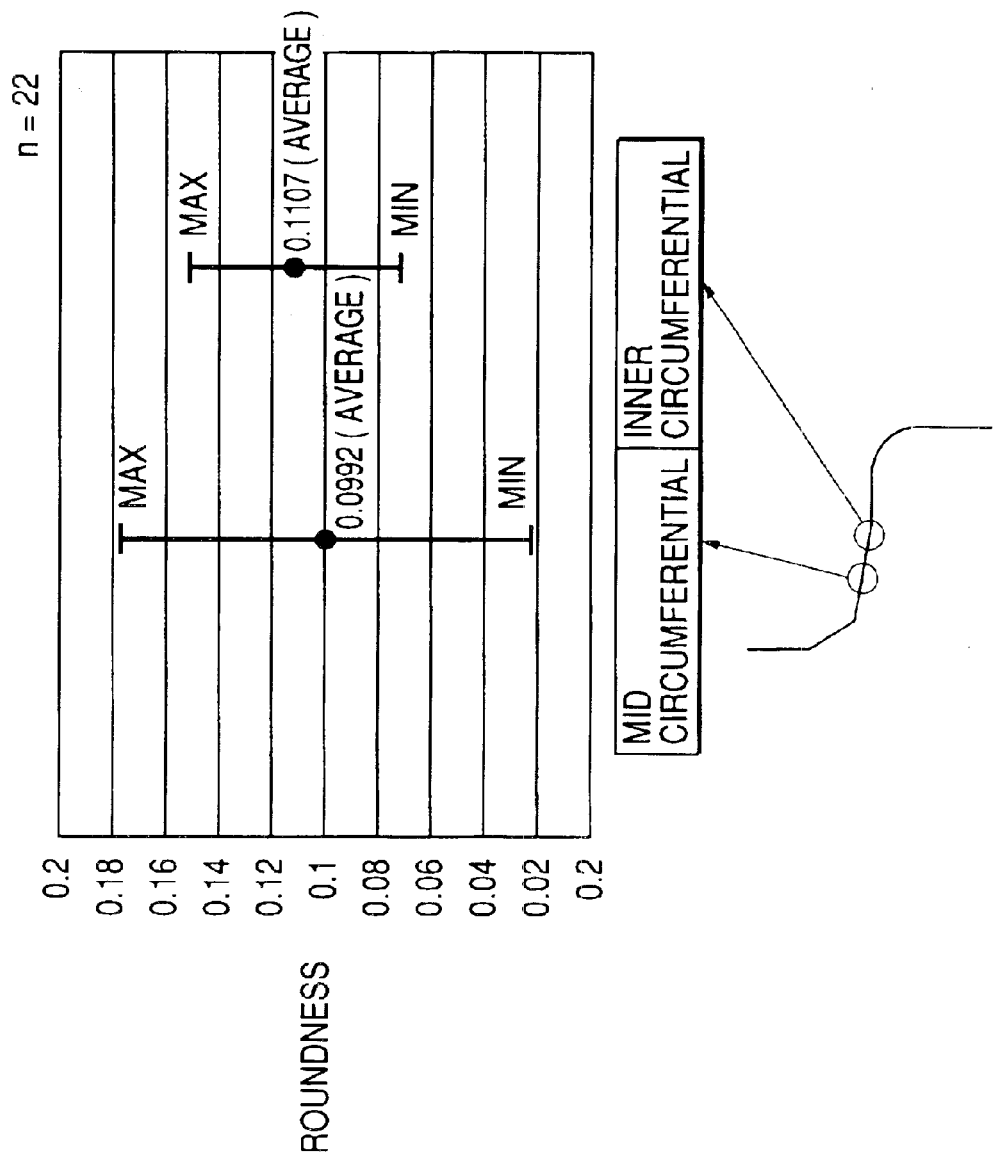
FIG. 13 is a graph showing the roundness of the tapered surface of the insulator located adjacent to the gas sensing element at an outer circumferential portion and at a mid circumferential portion in accordance with the third embodiment of the present invention.

FIG. 13 is a graph showing the roundness (i.e., calculated result with respect to the measured sizes) of the inner circumferential portion 332 based on the tested samples. FIG. 13 also shows the roundness of a mid circumferential portion (i.e., a reference circular portion passing the radial center) of the tapered surface 33.

As understood from the result shown in FIG. 13, the roundness of the inner circumferential portion 332 has a small dispersion. On the other hand, the roundness of the mid circumferential portion passing the radial center of the tapered surface 33 has a large dispersion.

Accordingly, the inner circumferential portion 332 has a better roundness compared with other region of the tapered surface 33. The inner circumferential portion 332 is brought into line contact with the metallic packing 11, thereby providing an excellent and stable sealing between them.

The rest of the gas sensor in accordance with the third embodiment is substantially the same as that of the gas sensor in accordance with the first embodiment. Thus, the third embodiment brings the same functions and effects as those of the first embodiment.

Fourth Embodiment

The gas sensor in accordance with a fourth embodiment is structurally similar to the gas sensor in accordance with the first embodiment, but is different in that an inclined upper surface of a metallic packing 11a serves as a receiving surface for supporting the pluglike insulator 3.

Figure 14:
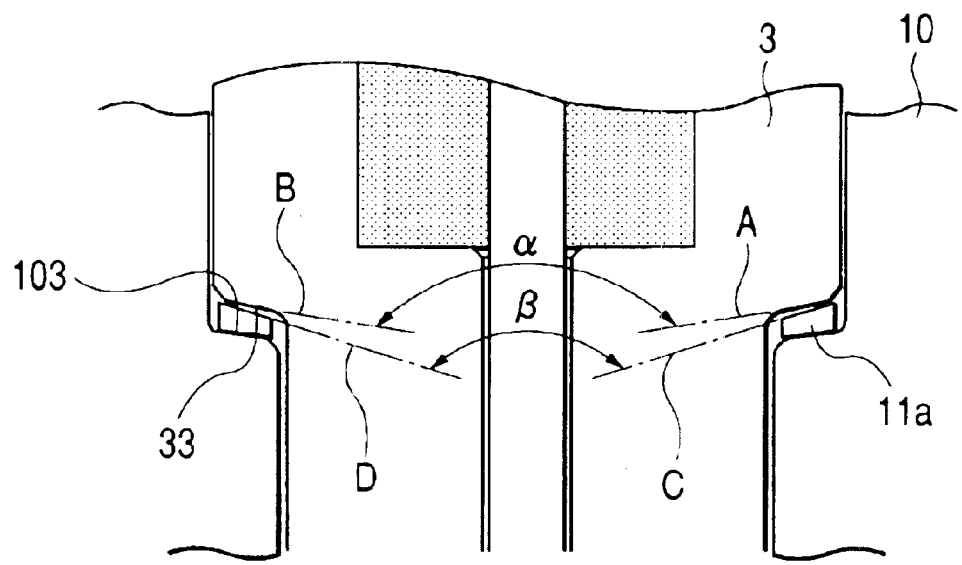
FIG. 14 is an enlarged cross-sectional view showing a relationship between the tapered surface angle $\beta$ and the receiving surface angle $\alpha$ in accordance with a fourth embodiment of the present invention.
Figure 15:
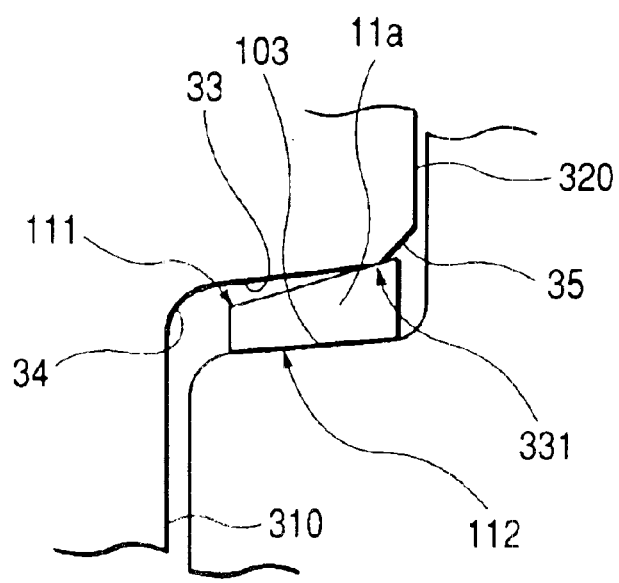
FIG. 15 is an enlarged cross-sectional view showing a sealing structure brought by a metallic packing interposed between the tapered surface and the receiving surface in accordance with the fourth embodiment of the present invention.
Figure 16:
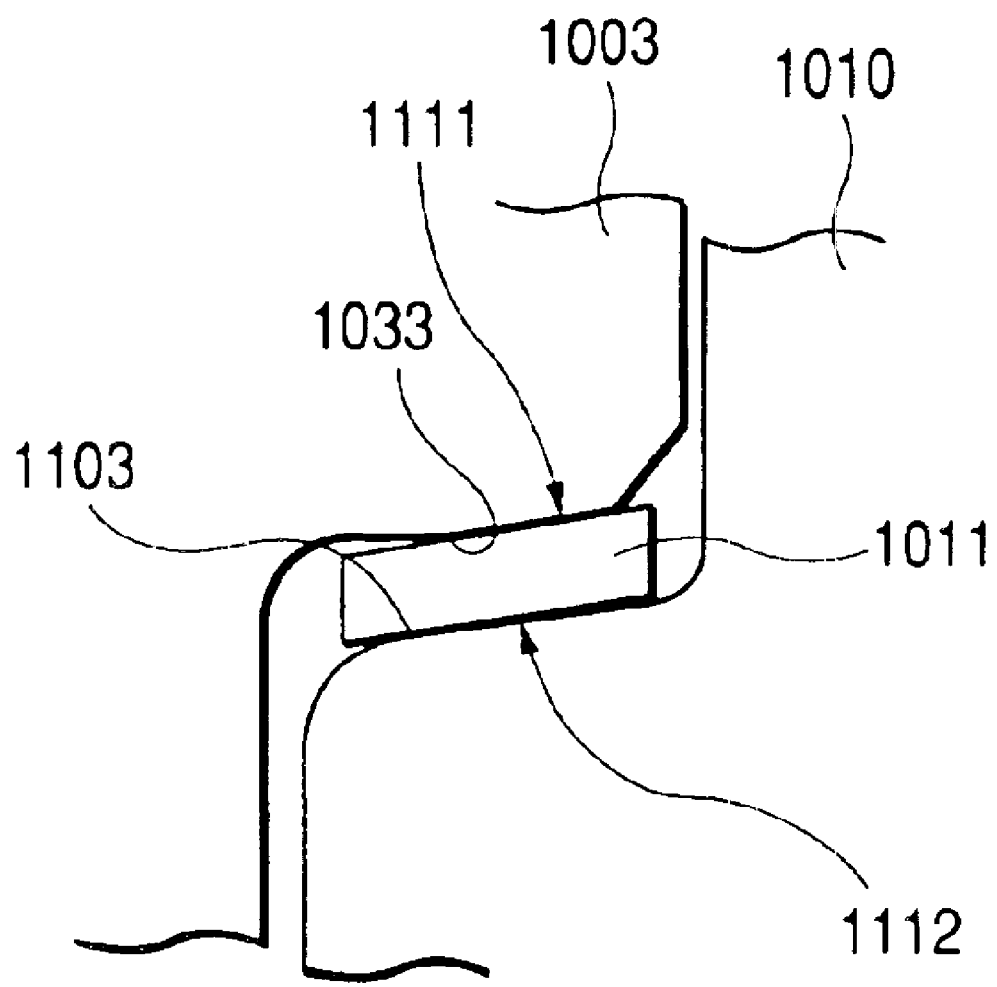
FIG. 16 is an enlarged cross-sectional view showing a sealing structure brought by a metallic packing interposed between a tapered surface and a receiving surface of a conventional gas sensor.

As shown in FIGS. 14 and 15, the tapered surface 33 of the pluglike insulator 3 extends from the large-diameter cylindrical surface 320 to the small-diameter cylindrical surface 310. The angle between the large-diameter cylindrical surface 320 and the tapered surface 33 is larger than 90° (i.e., α<180°). In other words, the tapered surface 33 protrudes outward (i.e., toward the distal end side of the insulator 3) with respect to the large-diameter portion 32. In this respect, the tapered surface 33 is referred to as being inclined in an axially outward direction.

More specifically, as shown in FIG. 14, the tapered surface 33 of the pluglike insulator 3 is in a non-parallel relationship with the upper surface 111 of the metallic packing 11a. The open angle α of the tapered surface 33, facing toward the proximal end side (i.e., upper direction) of the insulator 3, represents a crossing angle between two (right and left) inclined lines A and B of the tapered surface 33 in the cross-sectional view taken along the axis of the pluglike insulator 3 (i.e., along the axis of the gas sensing element 15). Similarly, the open angle β of the inclined upper surface 111 of metallic packing 11a, facing toward the proximal end side (i.e., upper direction) of the housing 10, represents a crossing angle between two (right and left) inclined lines C and D of the inclined upper surface 111 of metallic packing 11a in the cross-sectional view taken along the axis of the housing 10 (i.e., along the axis of the gas sensing element 15). According to the embodiment shown in FIG. 14, the open angle α of the tapered surface 33 is 160°. The open angle β of the inclined upper surface 111 of metallic packing 11a is 150°. The non-parallel relationship between the tapered surface 33 and the receiving surface (i.e., the inclined upper surface 111 of metallic packing 11a) is expressed by α>β and α−β=10°.

As shown in FIG. 15, the metallic packing 11a has a lower surface 112 which is brought into face-to-face contact with the receiving surface 103 of housing 10. The inclined upper surface 111 of metallic packing 11a is brought into line contact with an outer circumferential portion 331 of the tapered surface 33 of pluglike insulator 3.

Like the first embodiment shown in FIG. 2B, the outer circumferential portion 331 has substantially the complete roundness.

The rest of the gas sensor in accordance with the fourth embodiment is substantially the same as that of the gas sensor in accordance with the first embodiment. Thus, the fourth embodiment brings the same functions and effects as those of the first embodiment.

Functions and Effects Brought by Characteristic Features

As described above, the present invention provides a first gas sensor (1) including a gas sensing element (15) extending in a longitudinal direction of the gas sensor (1), a cylindrical insulator (3) having a through hole into which the gas sensing element (15) is airtightly inserted, and a cylindrical housing (10) airtightly supporting the cylindrical insulator (3) via an annular metallic packing (11). According to the first gas sensor (1), an annular receiving surface (103) is provided on an inner wall of the housing (10) to support the insulator (3) via the metallic packing (11). The annular receiving surface (103) extends in a radial direction with a predetermined inclined angle with respect to an axis of the gas sensing element (15). The insulator (3) has a small-diameter portion (31) and a large-diameter portion (32) which are continuously aligned in an axial direction of the insulator. A diameter of the large-diameter portion (32) is larger than a diameter of the small-diameter portion (31). An outer cylindrical surface of the insulator (3) includes a small-diameter cylindrical surface (310) extending in parallel with the axis of the gas sensing element (15), a tapered surface (33), and a large-diameter cylindrical surface (320) extending in parallel with the axis of the gas sensing element (15). The tapered surface (33) extends in a radially outer direction with a predetermined inclined angle with respect to the axis of the gas sensing element (15) from the small-diameter cylindrical surface (310) to the large-diameter cylindrical surface (320). And, an outer circumferential portion (331) of the tapered surface (33) is brought into line contact with the metallic packing (11) when the receiving surface (103) of the housing (10) supports the tapered surface (33) via the metallic packing (11).

The present invention provides a second gas sensor including a gas sensing element (15) extending in a longitudinal direction of the gas sensor (1), a cylindrical insulator (3) having a through hole into which the gas sensing element (15) is airtightly inserted, and a cylindrical housing (10) airtightly supporting the cylindrical insulator (3) via an annular metallic packing (11). According to the second gas sensor, an annular receiving surface (103) is provided on an inner wall of the housing (10) to support the insulator (3) via the metallic packing (11). The annular receiving surface (103) extending in a radial direction with a predetermined inclined angle with respect to an axis of the gas sensing element (15). The insulator (3) has a small-diameter portion (31) and a large-diameter portion (32) which are continuously aligned in an axial direction of the insulator. A diameter of the large-diameter portion (32) is larger than a diameter of the small-diameter portion (31). An outer cylindrical surface of the insulator (3) includes a small-diameter cylindrical surface (310) extending in parallel with the axis of the gas sensing element (15), a tapered surface (33), and a large-diameter cylindrical surface (320) extending in parallel with the axis of the gas sensing element (15). The tapered surface (33) extends in a radially outer direction with a predetermined inclined angle with respect to the axis of the gas sensing element (15) from the small-diameter cylindrical surface (310) to the large-diameter cylindrical surface (320). And, inner circumferential portion (332) of the tapered surface (33) is brought into line contact with the metallic packing (11) when the receiving surface (103) of the housing (10) supports the tapered surface (33) via the metallic packing (11).

The present invention provides a third gas sensor including a gas sensing element (15) extending in a longitudinal direction of the gas sensor (1), a cylindrical insulator (3) having a through hole into which the gas sensing element (15) is airtightly inserted, and a cylindrical housing (10) airtightly supporting the cylindrical insulator (3) via an annular metallic packing (11). According to the third gas sensor, an annular receiving surface (103) is provided on an inner wall of the housing (10) to support the insulator (3) via the metallic packing (11). The annular receiving surface (103) extends in a radial direction with a predetermined inclined angle with respect to an axis of the gas sensing element (15). The insulator (3) has a small-diameter portion (31) and a large-diameter portion (32) which are continuously aligned in an axial direction of the insulator. A diameter of the large-diameter portion (32) is larger than a diameter of the small-diameter portion (31). An outer cylindrical surface of the insulator (3) includes a small-diameter cylindrical surface (310) extending in parallel with the axis of the gas sensing element (15), a tapered surface (33), and a large-diameter cylindrical surface (320) extending in parallel with the axis of the gas sensing element (15). The tapered surface (33) extends in a radially outer direction with a predetermined inclined angle with respect to the axis of the gas sensing element (15) from the small-diameter cylindrical surface (310) to the large-diameter cylindrical surface (320). An outer circumferential portion (331) of the tapered surface (33) is brought into line contact with the metallic packing (11) when the receiving surface (103) of the housing (10) supports the tapered surface (33) via the metallic packing (11). And, a relationship between the tapered surface (33) and the receiving surface (103) is expressed by $\alpha > \beta$ and $0° < \alpha - \beta \leq 40°$ where $\alpha$ represents an open angle of the tapered surface (33) and $\beta$ represents an open angle of the receiving surface (103).

According to the first to third gas sensors of the present invention, the outer circumferential portion or the inner circumferential portion of the tapered surface has a better roundness compared with other region of the tapered surface. Accordingly, it becomes possible to bring the outer circumferential portion or the inner circumferential portion of the tapered surface into line contact with the metallic packing. An excellent and stable sealing is provided between them.

According to the first to third gas sensors, the cylindrical insulator (3) has the small-diameter portion (31) and the large-diameter portion (32) which are integrally made of a ceramic or comparable material. The tapered surface (33) is formed at a stepped portion formed between the small-diameter portion (31) and the large-diameter portion (32), as shown in FIGS. 1 to 4.

It is desirable to provide a curved or round corner (34) at a transitional point from the small-diameter portion (31) to the tapered surface (33). It is also preferable to provide a slant surface (35) at a transitional point from the tapered surface (33) to the large-diameter portion (32), as shown in FIG. 4.

The tapered surface (33) can be constituted as an annular plane extending perpendicularly to the axis of the gas sensor. The tapered surface (33) can be also constituted as an annular plane inclined with respect to the axis of the gas sensor. In the former case, the open angle $\alpha$ of the tapered surface (33) is 180°.

The outer circumferential portion (331) is in the corner portion (i.e., a transitional region) connecting the tapered surface (33) to the large-diameter cylindrical surface (320). When the corner portion is chamferred to form a slant surface, the outer circumferential portion (331) is located radially inside the large-diameter cylindrical surface (320), as shown in FIG. 4.

The inner circumferential portion (332) is in the corner portion (i.e., a transitional region) connecting the small-diameter cylindrical surface (310) to the tapered surface (33). When the corner portion is curved, the inner circumferential portion (332) is a terminal end of the corner portion located radially outside the small-diameter cylindrical surface (310), as shown in FIG. 12.

The metallic packing (11) is a ringlike member having a through hole into which the small-diameter portion (31) of the insulator (3) is inserted. The cross section of the metallic packing (11) consists of two rectangular regions symmetrical with respect to its axis. The upper surface (111) of the metallic packing (11) is brought into contact with the tapered surface (33) of the insulator (3). The lower surface (112) of the metallic packing (11) is brought into contact with the receiving surface (103) of the housing (10). It is preferable that the upper surface (111) is parallel to the lower surface (112). However, it is also possible to form the upper surface (111) and the lower surface (112) in a non-parallel relationship.

The housing (10) is a metallic cylindrical housing. The receiving surface (103) is provided on the inside wall of the housing (10). The receiving surface (103) is configured into a stepped portion protruding in a radially inward direction for supporting the insulator (3).

The gas sensing element (15) has a measured gas side electrode exposed to a measured gas and a reference electrode exposed to the air serving as a reference gas. The gas sensing element (15) produces an electric signal representing the concentration of a specific gas contained in the measured gas based on an ion current or an electric potential difference occurring between the measured gas side electrode and the reference electrode. The gas sensing element (15) consists of a plurality of solid electric substrates and insulating substrates being laminated so as to constitute a multilayered structure. It is preferable that the gas sensing element (15) integrally incorporates a heater.

The gas sensing element (15), for example, measures an oxygen concentration, a NOx concentration, a CO concentration, an HC concentration, or the like. It is also possible that the gas sensing element (15) simultaneously measures a plurality of different gas concentrations.

The first to third gas sensors are installed in the exhaust gas passage of an internal combustion engine of an automotive vehicle to control the combustion of the engine.

According to the third gas sensor, the open angle $\alpha$ of the tapered surface (33) and the open angle $\beta$ of the receiving surface (103) is expressed by $\alpha > \beta$ and $0° < \alpha - \beta \leq 40°$. Setting this relationship is effective to ensure the line contact between the outer circumferential portion (331) of the insulator (3) and the metallic packing (11), thereby providing an excellent and reliable sealing between them.

If the open angle difference ($\alpha - \beta$) exceeds 40°, the insulator (3) will excessively cut into the metallic packing (11) and will damage the metallic packing (11).

According to the third gas sensor, it is preferable that the open angle $\beta$ of the receiving surface (103) is in a range from 144° to 157° when the open angle $\alpha$ of the tapered surface (33) is 160°.

If the open angle $\beta$ is larger than 157°, the metallic packing (11) may be deformed undesirably and cannot maintain a satisfactory line contact and accordingly the sealing property will be worsened.

If the open angle $\beta$ is smaller than 144°, a force acting perpendicularly on the housing surface will decrease. In other words, a force for pressing the metallic packing (11) on the housing (10) becomes small. The loss will increase.

Furthermore, the contact area between the receiving surface (103) and the metallic packing (11) will become small, for example, due to a clearance appearing in the inner circumferential side of the metallic packing (11). This will reduce the sealable radial size and, as a result, will worsen the sealing property due to corrosion when the metallic packing (11) is subjected to the measured gas. Furthermore, this increases a surficial stress, i.e., a pressure acting on the lower surface (112) of the metal packing (11). A creep of the metallic packing (11) will occur.

More preferably, the open angle $\beta$ of the receiving surface (103) is in a range from 145° to 155°. The best range of the open angle $\beta$ of the receiving surface (103) is from 149° to 151° when the open angle $\alpha$ of the tapered surface (33) is 160°.

According to the first gas sensor, it is preferable that the tapered surface (33) of the insulator (3) is in a non-parallel relationship with the receiving surface (103) of the housing (10).

With this arrangement, the outer circumferential portion (331) of the insulator (3) is surely brought into line contact with the metallic packing (11) to provide a stable and excellent sealing between them.

It is also preferable that the tapered surface (33) of the insulator (3) protrudes in an axially outward direction with respect to the large-diameter portion (32), and the non-parallel relationship between the tapered surface (33) and the receiving surface (103) is expressed by $\alpha > \beta$ and $5° \leq \alpha - \beta \leq 20°$ where $\alpha$ represents the open angle of the tapered surface (33) and $\beta$ represents the open angle of the receiving surface (103).

As explained with reference to FIG. 3, the open angle ($\alpha$; $\beta$) faces the proximal end side of the gas sensor (1) and is defined as a crossing angle between two inclined lines (A, B; C, D) of an objective surface (33; 103) in a cross-sectional view taken along the axis of the gas sensing element (15).

When the tapered surface (33) of the insulator (3) protrudes in an axially outward direction with respect to the large-diameter portion (32), the angle between the large-diameter cylindrical surface 320 and the tapered surface 33 is larger than 90°. In other words, the open angle $\alpha$ is smaller than 180°, as understood from FIGS. 3, 11, and 14. Setting this relationship is effective to ensure the line contact between the insulator (3) and the metallic packing (11), thereby providing an excellent and reliable sealing between them.

If the open angle difference ($\alpha - \beta$) is less than 5°, the tapered surface (33) will be in substantially the parallel relationship with the receiving surface (103) and it will be difficult to provide a satisfactory line contact. If the open angle difference ($\alpha - \beta$) is larger than 20°, the force acting perpendicularly on the metallic packing (11) will decrease. In other words, the force for pressing the metallic packing (11) on the housing (10) becomes small. The sealing property will be worsened.

It is also preferable that the tapered surface (33) of the insulator (3) retracts in an axially inward direction with respect to the large-diameter portion (32), and the non-parallel relationship between the tapered surface (33) and the receiving surface (103) is expressed by $\alpha > \beta$ and $0° < \alpha - \beta \leq 40°$.

When the tapered surface (33) of the insulator (3) retracts in the axially inward direction with respect to the large-diameter portion (32), the angle between the large-diameter cylindrical surface 320 and the tapered surface 33 is smaller than 90°. In other words, the open angle $\alpha$ is larger than 180°, as understood from FIG. 9. Setting this relationship is effective to ensure the line contact between the insulator (3) and the metallic packing (11), thereby providing an excellent and reliable sealing between them.

If the open angle difference ($\alpha - \beta$) is larger than 40°, the insulator (3) will excessively cut into the metallic packing (11) and will damage the metallic packing (11).

Furthermore, it is preferable that the open angle $\beta$ of the receiving surface (103) is in the range from 144° to 157° when the open angle $\alpha$ of the tapered surface (33) is 160°.

If the open angle $\beta$ is larger than 157°, the metallic packing (11) may be deformed undesirably and cannot maintain a satisfactory line contact and accordingly the sealing property will be worsened.

If the open angle β is smaller than 144°, the force acting perpendicularly on the housing surface will decrease. In other words, the force for pressing the metallic packing (11) on the housing (10) becomes small. The loss will increase.

Furthermore, the contact area between the receiving surface (103) and the metallic packing (11) will become small, for example, due to a clearance appearing in the inner circumferential side of the metallic packing (11). This will reduce the sealable radial size and, as a result, will worsen the sealing property due to corrosion when the metallic packing (11) is subjected to the measured gas. Furthermore, this increases a surficial stress, i.e., the pressure acting on the lower surface (112) of the metal packing (11). A creep of the metallic packing (11) will occur.

More preferably, the open angle β of the receiving surface (103) is in a range from 145° to 155°. The best range of the open angle β of the receiving surface (103) is from 149° to 151° when the open angle α of the tapered surface (33) is 160°.

According to the second gas sensor, it is preferable that the tapered surface (33) of the insulator (3) is in a non-parallel relationship with the receiving surface (103) of the housing (10).

With this arrangement, the inner circumferential portion (332) of the insulator (3) is surely brought into line contact with the metallic packing (11) to provide a stable and excellent sealing between them.

It is also preferable that the tapered surface (33) of the insulator (3) protrudes in the axially outward direction with respect to the large-diameter portion (32), and the non-parallel relationship between the tapered surface (33) and the receiving surface (103) is expressed by α<β and $5° \leq \beta - \alpha \leq 40°$.

Setting this relationship is effective to ensure the line contact between the insulator (3) and the metallic packing (11), thereby providing an excellent and reliable sealing between them.

If the open angle difference (β−α) is less than 5°, the tapered surface (33) will be in substantially the parallel relationship with the receiving surface (103) and it will be difficult to provide a satisfactory line contact. If the open angle difference (β−α) is larger than 40°, the force acting perpendicularly on the metallic packing (11) will decrease. In other words, the force for pressing the metallic packing (11) on the housing (10) becomes small. The sealing property will be worsened.

It is preferable that a width of the line contact is in a range from 10 μm to 100 μm.

This assures a stable and excellent line contact between the insulator (3) and the metallic packing (10).

If the width of the line contact is less than 10 μm, the line contact between the tapered surface (33) and the metallic packing (11) will become unstable. If the width of the line contact is larger than 100 μm, the roundness of the line contact between the tapered surface (33) and the metallic packing (11) will be worsened locally. The sealing property will be dissatisfactory.

It is preferable that the line contact between the tapered surface (33) and the metallic packing (11) is annular, and at least 98% of the annular line contact is continuous.

Assuring the line contact being continuous along at least 98% of a complete circle is effective to provide a satisfactory sealing between the tapered surface (33) and the metallic packing (11), although it is needless to say that the best line contact is a complete circle.

If the line contact is less than 98% of a complete circle, the sealing property will be dissatisfactory.

It is preferable that a Vickers' hardness of the metallic packing (11) is in a range from 50 Hv to 200 Hv.

With this setting, the metallic packing (11) can deform adequately to eliminate undesirable clearances between the metallic packing (11) and the insulator (3) or the housing (10). Thus, it becomes possible to obtain an excellent sealing property.

When the receiving surface (103) of the housing (10) has an undulation, the metallic packing (11) having the Vickers' hardness in the range from 50 Hv to 200 Hv can deform along the undulated surface. Thus, it becomes possible to eliminate small clearances to be formed between the metallic packing (11) and the receiving surface (103) of the housing (10). The sealing property can be enhanced.

If the Vickers' hardness of the metallic packing (11) is less than 50 Hv, the metallic packing (11) is too soft to provide a stable line contact between the tapered surface (33) and the metallic packing (11).

If the Vickers' hardness of the metallic packing (11) is larger than 200 Hv, the metallic packing (11) is too hard to eliminate the undesirable clearances formed between the metallic packing (11) and the housing (10). The sealing property will be worsened.

The metallic packing (11) is made of a pure nickel member. However, it is possible to use a corrosion resistive material, such as titanium, nickel alloy, stainless, for forming the metallic packing (11). It is also possible to use a plated material, such as nickel or copper plated stainless.

Furthermore, it is preferable that the metallic packing (11) has a thickness of 0.1 mm or more. This setting provides a stable line contact and assures excellent sealing property.

It is preferable that the outer circumferential portion (331) or the inner circumferential portion (332) of the tapered surface (33) has an annular shape with the roundness equal to or less than 0.1, when the roundness is defined by (maximum diameter of annulus−minimum diameter of annulus)/2.

With this setting, the outer circumferential portion (331) or the inner circumferential portion (332) of the tapered surface (33) can be surely brought into line contact with the metallic packing (11). It this becomes possible to obtain excellent sealing between the insulator (3) and the metallic packing (11).

If the roundness is larger than 0.1, it will be difficult to obtain a stable line contact.

According to the above definition, the roundness is 0 when the circumferential portion has a complete roundness.

What is claimed is:

1. A gas sensor comprising:
    a gas sensing element extending in a longitudinal direction of said gas sensor;
    a cylindrical insulator having a through hole into which said gas sensing element is airtightly inserted; and
    a cylindrical housing airtightly supporting said cylindrical insulator via an annular metallic packing, wherein
    an annular receiving surface provided on an inside wall of said housing supports said insulator via said metallic packing, said annular receiving surface extending in a radial direction with a predetermined inclined angle with respect to an axis of said gas sensing element,
    said insulator has a small-diameter portion and a large-diameter portion which are continuously aligned in an axial direction of said insulator, an outer cylindrical surface of said insulator includes a small-diameter cylindrical surface extending in parallel with the axis of said gas sensing element, a tapered surface, and a large-diameter cylindrical surface extending in parallel with the axis of said gas sensing element, said tapered surface extends in a radially outer direction with a predetermined inclined angle with respect to the axis of said gas sensing element from said small-diameter cylindrical surface to said large-diameter cylindrical surface, an outer circumferential portion of said tapered surface being in line contact with one surface of said metallic packing, and said annular receiving surface of said housing is in face-to-face contact with the other surface of said metallic packing.

2. The gas sensor in accordance with claim 1, wherein said tapered surface of the insulator is in a non-parallel relationship with said receiving surface of said housing.

3. The gas sensor in accordance with claim 2, wherein said tapered surface of the insulator protrudes in an axially outward direction with respect to said large-diameter portion, and the non-parallel relationship between said tapered surface and said receiving surface is expressed by $\alpha > \beta$ and $5° \leq \alpha - \beta \leq 20°$ where $\alpha$ represents an open angle of said tapered surface and $\beta$ represents an open angle of said receiving surface.

4. The gas sensor in accordance with claim 2, wherein said tapered surface of the insulator retracts in an axially inward direction with respect to said large-diameter portion, and the non-parallel relationship between said tapered surface and said receiving surface is expressed by $\alpha > \beta$ and $0° < \alpha - \beta \leq 40°$ where $\alpha$ represents an open angle of said tapered surface and $\beta$ represents an open angle of said receiving surface.

5. The gas sensor in accordance with claim 1, wherein a width of said line contact is in a range from 10 $\mu$m to 100 $\mu$m.

6. The gas sensor in accordance with claim 1, wherein the line contact between said tapered surface and said metallic packing is annular, and at least 98% of the annular line contact is continuous.

7. The gas sensor in accordance with claim 1, wherein said outer circumferential portion of said tapered surface has an annular shape with a roundness equal to or less than 0.1, when said roundness is defined by (maximum diameter of annulus−minimum diameter of annulus)/2.

8. The gas sensor in accordance with claim 1, wherein said open angle $\alpha$ of said tapered surface represents a crossing angle between two inclined lines of said tapered surface in a cross-sectional view taken along the axis of said gas sensing element, and said open angle $\beta$ of said receiving surface represents a crossing angle between two inclined lines of said receiving surface in the cross-sectional view taken along the axis of said gas sensing element.

9. The gas sensor in accordance with claim 1, wherein the metal packing is formed from a corrosion resistive material select from the group consisting of titanium, nickel, nickel alloy, stainless steel, nickel plated stainless steel, and copper plated stainless steel.

10. The gas sensor in accordance with claim 9, wherein the metallic packing is made of a pure nickel member.

11. The gas sensor in accordance with claim 1, wherein the metal packing has a thickness of 0.1 mm or more.

12. The gas sensor in accordance with claim 1, wherein a Vickers' hardness of said metallic packing is in a range from 50 Hv to 200 Hv.

* * * * *